United States Patent
Snow et al.

(10) Patent No.: US 7,776,269 B2
(45) Date of Patent: *Aug. 17, 2010

(54) CAPACITIVE BASED SENSING OF MOLECULAR ADSORBATES ON THE SURFACE OF SINGLE WALL NANOTUBES

(75) Inventors: Eric S. Snow, Springfield, VA (US); F. Keith Perkins, Alexandria, VA (US); Eric Houser, Nokesville, VA (US); Stan V. Stepnowski, Alexandria, VA (US); R. Andrew McGill, Lorton, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 755 days.

This patent is subject to a terminal disclaimer.

(21) Appl. No.: 11/239,430

(22) Filed: Sep. 27, 2005

(65) Prior Publication Data
US 2006/0249402 A1    Nov. 9, 2006

Related U.S. Application Data

(60) Provisional application No. 60/662,464, filed on Mar. 15, 2005.

(51) Int. Cl.
G01N 27/00 (2006.01)
G01N 27/02 (2006.01)
G01N 27/04 (2006.01)
G01N 27/12 (2006.01)
G01N 33/00 (2006.01)
G01N 33/48 (2006.01)
G01N 33/53 (2006.01)

(52) U.S. Cl. .......... 422/82.01; 422/68.1; 422/82.02; 422/82.03; 422/82.04; 435/4; 436/149; 977/702; 977/742; 977/920

(58) Field of Classification Search .......... 422/68.01, 422/82.01–82.04
See application file for complete search history.

(56) References Cited

U.S. PATENT DOCUMENTS 3,491,293 A * 1/1970 Seaborn, Jr. ............... 324/713

(Continued)

FOREIGN PATENT DOCUMENTS

JP        08036020 A  *  2/1996

(Continued)

OTHER PUBLICATIONS

Nylander, "Chemical and biological sensors," J. Phys. E: Sci. Instrum., 1995, vol. 18, pp. 736-750.*

(Continued)

*Primary Examiner*—Unsu Jung
(74) *Attorney, Agent, or Firm*—Amy L. Ressing; Joseph T. Grunkemeyer (57) ABSTRACT

A sensing device having: a bottom electrode, a dielectric on the bottom electrode, a grid of nanoelectrodes on the dielectric, and a top electrode in electrical contact with the grid. A method of chemical or biological sensing comprising: providing a grid of nanoelectrodes; exposing the grid to fluid suspected of containing a chemical or biological analyte; and measuring a change in the capacitance and conductance of the grid.

19 Claims, 7 Drawing Sheets

U.S. PATENT DOCUMENTS

| | | | |
|---|---|---|---|
| 5,010,773 A * | 4/1991 | Lorenz et al. | 73/862.041 |
| 5,859,443 A * | 1/1999 | Yamazaki et al. | 257/65 |
| 6,207,580 B1 * | 3/2001 | Costaganna | 438/712 |
| 6,252,262 B1 * | 6/2001 | Jonker et al. | 257/192 |
| 6,278,231 B1 * | 8/2001 | Iwasaki et al. | 313/310 |
| 6,528,020 B1 * | 3/2003 | Dai et al. | 422/98 |
| 6,918,284 B2 * | 7/2005 | Snow et al. | 73/31.05 |
| 2004/0110277 A1 * | 6/2004 | Maeda | 435/287.2 |
| 2004/0132070 A1 * | 7/2004 | Star et al. | 435/6 |
| 2004/0192072 A1 * | 9/2004 | Snow et al. | 438/800 |

FOREIGN PATENT DOCUMENTS

WO     WO 2004044586 A1 *    5/2004

OTHER PUBLICATIONS

Patel et al, "Chemicapacitive Microsensors for Volatile Organic Compound Detection", Sensors and Actuators B, 2003, vol. 96, pp. 541-553.

Snow et al, "Random Networks of Carbon Nanotubes as an Electronic Material", Applied Physics Letters, Mar. 2003, vol. 82, No. 13, pp. 2145-2147.

Kong et al, "Nanotube Molecular Wires as Chemical Sensors", Science, Jan. 2000, vol. 287, pp. 622-625.

Novak et al, "Nerve Agent Detection Using Networks of Single-Walled Carbon Nanotubes", Applied Physics Letters, Nov. 2003, vol. 83, No. 19, pp. 4026-4028.

* cited by examiner

CAPACITIVE BASED SENSING OF MOLECULAR ADSORBATES ON THE SURFACE OF SINGLE WALL NANOTUBES

The application claims the benefit of U.S. Provisional Patent Application No. 60/662,464 filed on Mar. 15, 2005, incorporated herein by reference.

BACKGROUND OF THE INVENTION

1. Field of the Invention

The invention relates generally to the field of sensors.

2. Description of the Related Art

Sorption-based microsensors are currently a leading candidate for low-power, compact chemical vapor detection for defense, homeland security, and environmental monitoring applications. Such a sensor combines a nonselective transducer with a chemoselective material that serves as a vapor concentrator resulting in a highly sensitive detector that responds selectively to a particular class of chemical vapor. An array of such sensors, each coated with a different chemoselective material, produces a response fingerprint that can detect and identify an unidentified analyte. Sorption-based sensors provide sensitive detection for vapors ranging from volatile organic compounds to semi-volatile chemical nerve agents, although low-vapor-pressure materials such as explosives are challenging because they do not produce a sufficiently high concentration of vapor.

The transducer elements for such sensor arrays need to be small, low power, and compatible with conventional microprocessing technology. Among the choices of transducers are chemicapacitors that detect changes in dielectric properties, microresonators that detect changes in mass and viscoelastic properties of the chemoselective coating during analyte exposure, and chemiresistors that monitor the resistance of a conductive polymer or polymer composite. Chemiresistors are simple to implement, but can suffer from instability of the conductive particle/polymer interface, slow response and insufficient sensitivity. Microresonators can suffer from instability in the resonator-coating interface and are higher power devices. Chemicapacitors are more stable but can suffer from slow response. As with chemiresistors, this slow response is a result of the time necessary to load and then remove the analyte from the relatively thick layers of chemoselective material (~1 μm) that are typically used.

In a typical geometry for a commercial capacitance-based chemical sensor (Seacoast Sciences Inc.), the top electrode is a suspended grid of lithographically defined metal wires or a perforated membrane that allows chemical/biological analytes to pass between the wires into the active region of the capacitor. The sorbent layer between the top and bottom electrodes is a chemoselective material that selectively absorbs a class of chemical or biological analyte. Upon absorption of the analyte the dielectric properties of the chemoselective material are modified, which in turn produces a change in capacitance between the top grid and bottom planar electrodes. The capacitance, C, is measured by applying an AC voltage, $V_{AC}$, to the device and detecting the AC current $I_{AC} = \omega C V_{AC}$ where $\omega$ is the AC frequency.

Such a transduction mechanism is highly stable; however, the analyte must diffuse laterally through the polymeric dielectric a distance that is comparable to the lithographic linewidth in order to produce a maximum signal. In order to maintain a low fabrication cost the minimum linewidth of the top capacitor plate is ~1 μm. Consequently, this lateral diffusion, driven by a concentration gradient, results in a long response time (~minutes) and limits the sensitivity.

The unique structural and electrical properties of single-walled carbon nanotubes (SWNTs) have inspired researchers to investigate and develop SWNT-based chemical and biological sensors. Initial work in this area has shown that the resistance of SWNTs changes in response to the exposure to certain molecules that undergo a charge transfer upon adsorption on the SWNT surface (Kong et al., "Nanotube Molecular Wires as Chemical Sensors", *Science*, 87, 622 (2000). All reference publications and patents are incorporated herein by reference). Such SWNT-based chemiresistors have been used to detect both toxic industrial chemicals and a simulant for chemical nerve agents. In addition, by incorporating random networks of SWNTs as the active sensor element such sensors can be manufactured using conventional microfabrication techniques (Novak et al., "Nerve agent detection using networks of single-walled carbon nanotubes", *Appl. Phys. Lett.*, 83, 4026 (2003); Snow et al., "Random networks of carbon nanotubes as an electronic material", *Appl. Phys. Lett.*, 82, 2145 (2003)), circumventing the need for precise assembly. However, SWNT chemiresistors also exhibit several undesirable properties such as a high level of 1/f noise, slow recovery, and a susceptibility to contact effects.

SUMMARY OF THE INVENTION

The invention comprises a sensing device comprising: a bottom electrode, a dielectric on the bottom electrode, and a grid of nanoelectrodes on the dielectric, and a top electrode in electrical contact with the grid.

The invention further comprises a method of chemical or biological sensing comprising: providing a grid of nanoelectrodes, exposing the grid to fluid suspected of containing one or more chemical or biological analytes, and measuring a change in the capacitance of the grid.

BRIEF DESCRIPTION OF THE DRAWINGS

A more complete appreciation of the invention will be readily obtained by reference to the following Description of the Example Embodiments and the accompanying drawings.

DETAILED DESCRIPTION OF THE EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Disclosed herein is an alternative capacitance-based or multi-modal sensor that can eliminate the lateral diffusion limited process and instead relies upon the capacitance-based and optionally conductance-based detection of analyte molecules that are adsorbed directly onto or near to the surface of a grid of nanometer-diameter electrodes. In this configuration a voltage applied between the top grid and the bottom planar electrode produces large fringing electric fields radiating outward from the nanoelectrodes. This high field induces a polarization of any analyte molecules adsorbed onto or in the immediate vicinity of the surface of the nanoelectrodes, which produces an easily measured increase in capacitance. Similarly, a voltage applied between two otherwise isolated contacts to the nanoelectrode grid can induce a current to flow between the two contacts. This current is modified by a change in conductance of the grid, which may be induced by (among other things) electrical charge transfer between the grid and analyte molecules in the immediate vicinity of the nanoelectrodes.

The invention can include capacitance measurements on single-walled carbon nanotubes (SWNTs) in the presence of chemical vapors. Under bias the large fringing electric fields radiating from a network of SWNTs polarize molecular adsorbates, which is detected as a change in capacitance. These measurements provide an experimental tool for investigating the properties of chemical adsorbates. Such capacitors can also be configured as high-performance chemical sensors by coating the SWNTs with chemoselective polymers that provide large, class-specific gain to the capacitance response. Such chemicapacitors can be fast, highly sensitive, and completely reversible.

The capacitance response of the SWNT chemicapacitor may be dominated by surface adsorbates, which allows use of very thin layers of chemoselective material down to, and including, a single molecular monolayer. By achieving chemical selectivity with such a monolayer, the time required to load and refresh a thicker, chemoselective dielectric is eliminated and sensitive, real-time sensing can be performed.

The surface capacitance effect is caused by the large electric field gradient radiating from the ~1 nm-diameter SWNT electrodes. This transduction mechanism is quite general and can be used to detect volatile organics and low-vapor-pressure explosives. The transducer may be compatible with conventional chemoselective polymers by using a hydrogen-bonding polymer to achieve a minimum detectable level (MDL) of 0.5 part-per-billion (ppb) for dimethylmethylphosphonate (DMMP), a simulant for the chemical nerve agent sarin.

In comparison to other adsorption-based capacitance sensors, high sensitivity is achieved with a fast response time. Such other sensors are limited by the diffusion and loading through a thick (~1 μm) polymer dielectric that is sandwiched between a bottom planar electrode and a microfabricated metal grid. In principle, the polymer coating of a SWNT capacitance sensor can be reduced to a thickness on the order of the SWNT diameter, or applied as a molecular monolayer directly to the SWNT surface itself. Thus, it may be possible to achieve near instantaneous response times with minimal loading.

Figure 1:
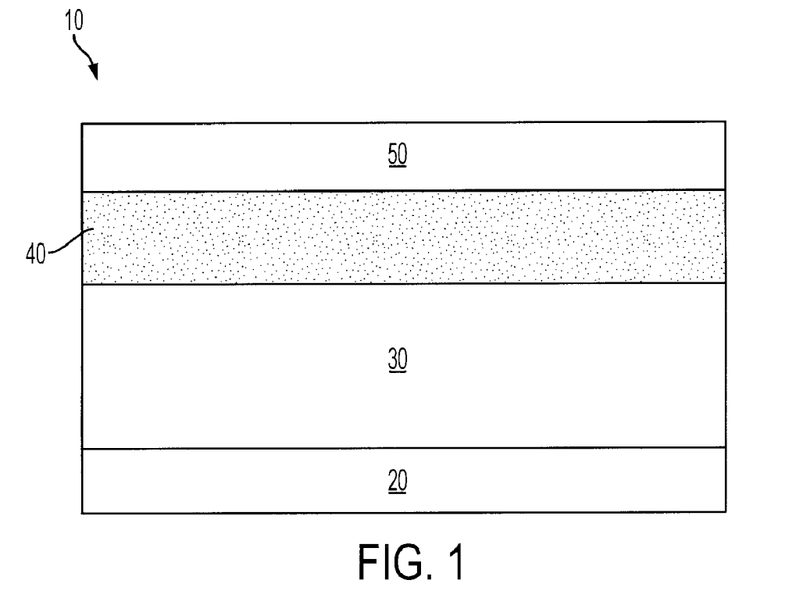
FIG. 1 schematically illustrates a sensing device or portion thereof.

At a minimum, the sensing device 10 comprises a bottom electrode 20, a dielectric 30, a grid of nanoelectrodes 40, and a top electrode 50, a cross-section of which is schematically illustrated in FIG. 1. Use of the terms "bottom" and "top" does not imply that the sensor must be in any particular orientation. In some embodiments the grid of nanoelectrodes is an interconnected grid of carbon nanotubes, including but not limited to single-walled carbon nanotubes.

Figure 2:
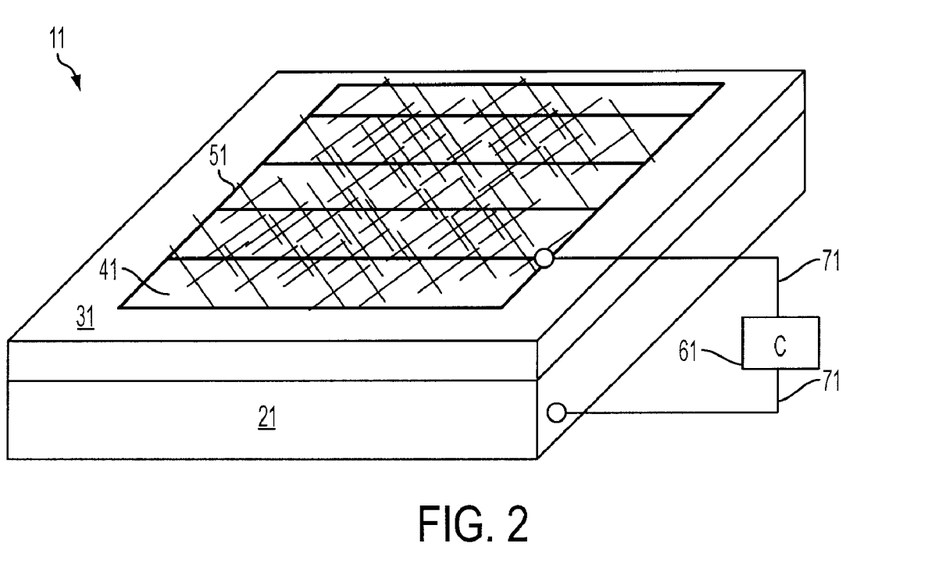
FIG. 2 schematically illustrates an embodiment of the sensor using a capacitance meter.

In one embodiment 11 schematically illustrated in FIG. 2, a capacitance meter 61 is electrically connected to the top electrode 51 and the bottom electrode 21 by leads 71. That the nanoelectrodes 41 on the dielectric 31 are shown at right angles is illustrative. The nanoelectrodes may be at any angles, including but not limited to random angles. The configuration of the top electrode 51 is illustrative only and may be in other configurations. A top electrode comprised of connected leads as shown, as opposed to a solid planar electrode, allows for access to the grid by the sample. The capacitance meter may be a single instrument or may comprise a separate AC voltage source and AC ammeter.

When the sensor is exposed to fluid such as air, water, blood, hydraulic fluid, factory plume, or any other suitable gas or liquid suspected of containing a biological or chemical analyte, adsorption of such analyte may cause a change in the capacitance of the grid of nanoelectrodes. The capacitance meter is used to measure this change in capacitance and the change may be correlated to the concentration of the analyte in the air.

The nanoelectrodes may be a network of carbon nanotubes as disclosed in, but not limited to Snow et al., U.S. Pat. No. 6,918,284, incorporated herein by reference. As used and claimed herein, the term "network" also includes a plurality of nanoelectrodes, such as carbon nanotubes, that each span a gap between two electrodes without or without necessarily intersecting each other. This configuration may be known as aligned nanotubes. The SWNTs may be ≈1 nm in diameter as grown and can be easily deposited or grown into an electrically conducting two-dimensional network that can cover arbitrarily large areas and can be fabricated into sensors using conventional microfabrication technology. In the presence of a chemical vapor, attractive interactions between the analyte and the SWNTs can concentrate the analyte on their surface. Without limiting the scope of the claims to any particular mechanism, under bias the fringing electric field that radiates from the SWNT electrode can produce a net polarization of the analyte that is detected as an increase in the capacitance. Because the SWNTs are ~1 nm in diameter the electric field drops rapidly within a few nanometers of the surface. This large field gradient coupled with the high density of analyte molecules on the surface results in a capacitance response that is dominated by surface adsorbates. Because most molecular adsorbates produce a weak, nonspecific interaction with the SWNT surface, the capacitors rapidly respond to a broad spectrum of molecular adsorbates and can serve as a general-purpose transducer for detecting chemical vapors. In comparison to the resistance response the SWNT capacitors are faster, more sensitive, and more reliable.

Other components of the sensor may also affect the change in capacitance. The dielectric constant of the dielectric layer may be affected by adsorption of the analyte. This change may be made more prominent by using a porous dielectric. Additional materials may also be added to the sensor, including but not limited to, a chemoselective or bioselective collection material deposited on the carbon nanotubes, a chemoselective or bioselective filter deposited on the carbon nanotubes that prevents one or more compounds from contacting the carbon nanotubes, and a chemoselective or bioselective functionalizing material that affects the surface chemistry of the carbon nanotubes.

The fact that most molecular adsorbates produce a capacitance response indicates that this transduction mechanism can be used to detect a broad spectrum of molecular analytes. However, in order to realize a practical sensor chemical specificity may be imparted to the sensor response. To provide chemical selectivity to the sensors, application of sorption-based chemoselective materials may be used. The SWNT networks may be coated with a thin film of a chemoselective polymer. The polymer highly concentrates a particular class of chemical vapor in the vicinity of the SWNTs and produces a large class-specific gain to the capacitance response. The resulting sensors may be fast, sensitive, and reversible. Surface reaction of organosilanes and deposition of thin polymer films may be used. Organosilanes, in particular the alkylsilanes methyl trimethoxysilane or trimethylchlorosilane, can have the expected effect of reducing the affinity of an oxide substrate to water and similar species without apparently modifying the SWNT response. By using arrays of such surface treated and polymer-functionalized SWNT chemicapacitors, a response "fingerprint" can be obtained in order to detect and identify the vapors of toxic industrial chemicals, explosives and chemical warfare agents.

Figure 3:
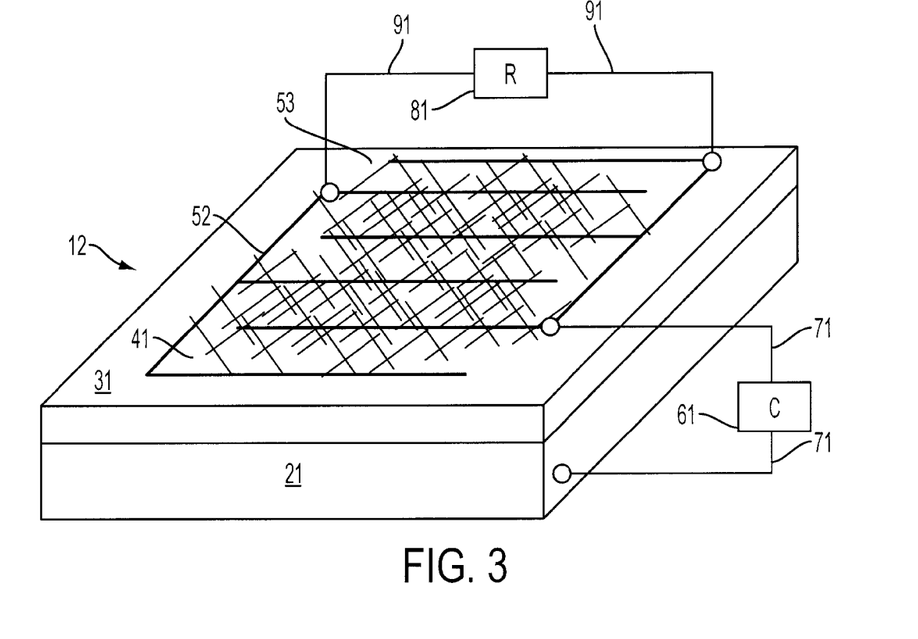
FIG. 3 schematically illustrates an embodiment of the sensor using a capacitance meter and an ohmmeter.

Another embodiment 12 is schematically illustrated in FIG. 3. In this embodiment, the top electrode is made up of a first top electrode 52 and a second top electrode 53. Both are in electrical contract with a grid of nanoelectrodes such as SWNTs, but are not in direct physical contact with each other. The two top electrodes are illustrated as interdigitated electrodes, however other configurations may be used. In this embodiment, an ohmmeter 81 is electrically connected to both top electrodes 52, 53 by leads 91, in addition to the capacitance meter 61. The ohmmeter may be a single instrument or may comprise a separate voltage source and ammeter. The resistance can be measured with a DC voltage or with an AC voltage by using a different frequency than the capacitance measurement. The use of AC voltage may improve the signal to noise ratio. The capacitance meter may be connected to the first top electrode or the second top electrode.

In this embodiment, adsorption of the analyte may also change the resistance of the grid, which may be measured by the ohmmeter. The changes in both the resistance and the capacitance may together be correlated to the identity of an analyte. The resistance of SWNTs changes in response to certain molecular species that undergo a charge transfer interaction with the SWNT upon adsorption. This resistive transduction mechanism may have a different physical origin than the capacitance-based transduction. This combined sensing technique can provide two orthogonal transduction mechanisms in the same sensor, which can be used as an additional tool for analyte identification. For example, the ratio of the conductance (derived from the resistance) to the capacitance sensor responses may be a measure of an intrinsic property of an analyte that is independent of concentration that may aid in identification.

Figure 4:
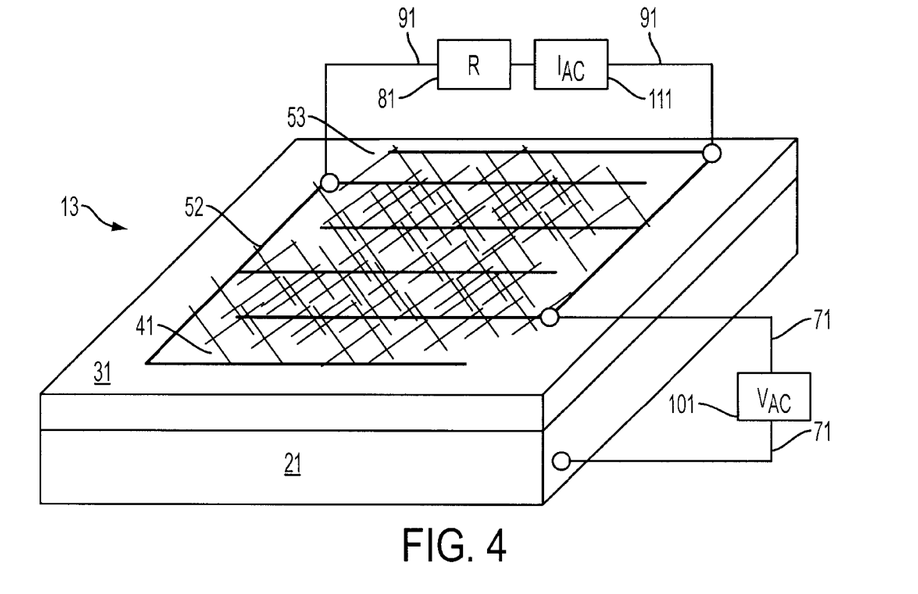
FIG. 4 schematically illustrates an embodiment of the sensor using transistor transconductance.

Another embodiment 13 is schematically illustrated in FIG. 4. This embodiment differs from the previous one by using an AC voltage source 101 instead of the capacitance meter and additionally an AC ammeter 111 electrically connected to the first top electrode and the second top electrode. The change in the capacitance from interaction with analyte correlates to a change in the AC current between the two top electrodes. As in the previous embodiment, the changes in both the resistance and the capacitance may together be correlated to the identity of an analyte. The ohmmeter 81 is not necessary for measuring the capacitance. Also, a capacitor may be replace one of leads 91.

In this embodiment, the dielectric constant, $\in$, is measured indirectly by modulating the conductance of the SWNTs via a capacitively coupled gate electrode. Capacitance scales as the area of the device. Therefore, a direct capacitance measurement requires a relatively large device area in order to produce an easily measured capacitance signal, i.e. $I_{AC}=\omega C V_{AC}$. However, SWNTs are electrically active (i.e. the conductance can be varied using a gate voltage) and the SWNT nanoelectrodes can be configured as the active electronic material in a transistor configuration. In this configuration the capacitance is detected via a measurement of the transistor transconductance, $g_m \equiv dI_{SD}/dV_G$, which is proportional to $\in$. An advantage of this configuration is that for a fixed aspect ratio (i.e., length to width ratio of the active sensing area between the two electrodes) the measured signal, $dI_{SD}/dV_G$, is independent of the device area so that the sensor can be made arbitrarily small without a reduction of signal.

The sensor may have a number of advantages. The response and recovery of the sensor can be very fast (governed by the analyte desorption time). The response time of conventional C sensors can be several minutes and is determined by the diffusion time of the analyte through ~1 μm of a chemoselective dielectric medium. However, the measured response time (~1 s) of this system is limited by the vapor delivery system used.

The sensor detects the physisorption of analyte molecules on the SWNTs. When the analyte source is removed the molecules may quickly desorb from the surface and the sensor returns to its quiescent state. For practical purposes SWNTs are chemically inert (graphite), which can make the detection process completely reversible. The sensor may rapidly return to its initial state after repeated exposures to a large number of different analytes with no degradation in the sensor response. In the few cases in which desorption from the surface is less rapid (e.g. ammonia), brief heating has been found to accelerate return of the sensor to the initial state.

The sensor response to ≈20 different vapors has been tested, and it has been established that for many analytes the sensor response is proportional to (% saturated vapor)×(analyte dipole moment). Many other analytes with no permanent dipole moment (e.g. hexane) are also capable of inducing a finite and repeatable sensor response. This is attributed to an inherent polarizability, in which a dipole moment is induced by the high electric field in the vicinity of the nanoelectrodes. Consequently, this transduction mechanism is applicable to a broad range of analytes.

Conventional chemicapacitors require a multilevel fabrication process at a MEMs foundry to produce the capacitor. The nanoelectrode fabrication can be an inexpensive, simple, one-step process of either deposition or direct growth of the SWNTs on the substrate followed by deposition of metal contacts.

The sensor response may be relatively insensitive to fluctuations in the CNT deposition process. Consequently, device-to-device reproducibility can be high and the response can be quantitatively predicted.

Sensitivity and response times may be significantly improved with a few design modifications. The sensitivity is currently limited by the small series capacitance of the thick $SiO_2$ layer. By thinning the $SiO_2$ layer or replacing it with a high-κ-dielectric insulator, it is estimated that the series capacitance can be increased by about a factor of 10, which should produce a comparable increase in response.

Figure 14:
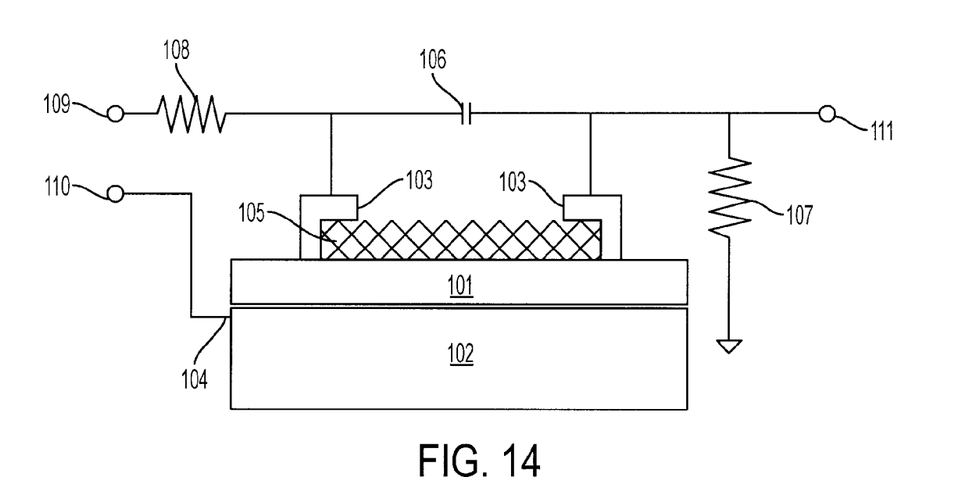
FIG. 14 shows a sample circuit using the sensor.

A sample circuit incorporating the sensor is illustrated in FIG. 14. The nanotube network 105 is on a thin oxide insulating layer 101 on a conductive substrate 102. Ohmic contacts 103 connect the network 105 to circuit elements including parallel capacitor 106, bias resistor 107, series resistor 108, and connections to conductance measurement signal generator 109 and to conductance and capacitance meters (high Z) 111. Ohmic contact 104 connects the substrate 102 to connection to capacitance measurement signal generator 110.

Having described the invention, the following examples are given to illustrate specific applications of the invention. These specific examples are not intended to limit the scope of the invention described in this application.

EXAMPLE 1

General procedure for growth of nanotube films and formation of top electrode—Select the desired substrate such as heavily doped silicon wafers with a thick thermal oxide, which may or may not be thinned to achieve a target, specific thickness. Alternatively, lightly doped silicon with patterned heavily doped areas may be used to isolate devices from one another. Alternatively, very thin, free-standing, supported films may be used.

Clean the substrate. While there exist many well-established methods of cleaning, treatment with a $CO_2$ snow-jet process may have advantages. The function of this process, in addition to mechanical cleaning, is to charge the insulating surface.

Deposit a thin, sparse layer of growth catalyst on the surface. One process uses a solution of catalyst in alcohol:
a. Prepare the catalyst solution. The catalyst solution used here is a mixture of 14 mg $FeNO_3:(H_2O)_9$ in 80 mL isopropyl alcohol, stirred for at least 2 hours but generally not longer than 24 hours.
b. Dip the substrate into the catalyst solution for about 10 seconds.
c. Upon removing, before it dries, rinse the substrate with hexane.
d. Blow dry with inert gas.

Other procedures for depositing growth catalyst crystals work as well, even vapor deposition.

Load the substrate into a suitable furnace, such as a tube furnace. Other geometries may work.

Grow the nanotubes. Other procedures have been used and give similar results. This will grow a random interconnected network comprising a mixture of metallic and semiconducting nanotubes:
a. After purging the furnace and gas lines well, bring the furnace and substrate to the growth temperature (800° C.) while flowing a mixture of inert and reducing gases.
b. Induce growth by flowing a mixture of Ar at 600 ccm, $H_2$ at 400 ccm, and ethylene at 5 ccm through the tube across the hot sample for 20 minutes.
c. Cool under an inert gas flow.

Deposit a patterned layer of metal across the substrate and nanotube network to form the desired electrodes. One pattern is a compromise among several performance requirements, including but not limited to the following:
a. Area of detector
b. Size of electrode(s)
c. Network resistance
d. Aspect ratio of active area
e. Detector parasitic capacitance
f. Detector circuit topology
g. Electrode-network contact resistance E-beam evaporation was used here to deposit a 5-10 nm Ti film followed by a 100 nm Au film, and a lift-off deposition process.

Remove nanotubes from where they are not wanted. Mask areas of the surface where it is desired to keep the nanotube network, such as with a photoresist pattern. Remove or destroy the nanotubes by one of several methods, including but not limited to: a $CO_2$ snow jet; a brief, mild $O_2$ plasma; and an aqueous oxidizing solution. Remove the photoresist in an appropriate solvent. It is also possible to pattern the initial catalyst deposition to achieve an equivalent result, thus obviating this step.

Make an electrical contact to the substrate. This may be accomplished by selective removal of surface oxide and subsequent metal deposition, or contact to the back side of the die.

EXAMPLE 2

Capacitance measurement—SWNT chemicapacitors were fabricated by using chemical vapor deposition to grow a SWNT network on a 250 nm-thick thermal oxide on a highly doped silicon substrate. For each sensor a 2 mm×2 mm interdigitated array of Pd electrodes was deposited on top of the SWNT network by using photolithography and lift-off. The interdigitated electrodes provided contacts for the simultaneous measurement of both the capacitance and the resistance of the SWNT network. The region inside the array was protected by photoresist and the unprotected SWNTs were removed from the substrate by a $CO_2$ snowjet. The photoresist was then removed exposing the SWNT network to the ambient environment. The chemical vapors were prepared by mixing saturated vapors of the analyte with dry air, and the concentrations are reported as a fraction of the equilibrium vapor pressure, $P/P_0$.

The SWNT network formed an array of nanoscale electrodes that served as one plate of the chemicapacitor with the other electrode formed by the heavily doped Si substrate. The capacitance of the device was measured by applying a 30 kHz, 0.1 V AC voltage between the electrodes and detecting the out-of-phase AC current with a lock-in amplifier. The measured capacitance, 10 $nF/cm^2$, was close to the parallel plate value corresponding to a 250 nm-thick $SiO_2$ gate dielectric. For SWNT networks with an inter-nanotube spacing smaller than the $SiO_2$ thickness, the capacitance will approximate that of a parallel-plate capacitor because of the overlapping field lines of neighboring SWNTs. Note that the capacitance response in the present sensor is limited by the small series capacitance of the thick $SiO_2$ layer. This series capacitance may be increased by at least an order of magnitude producing a comparable increase in signal-to-noise.

Figure 5:
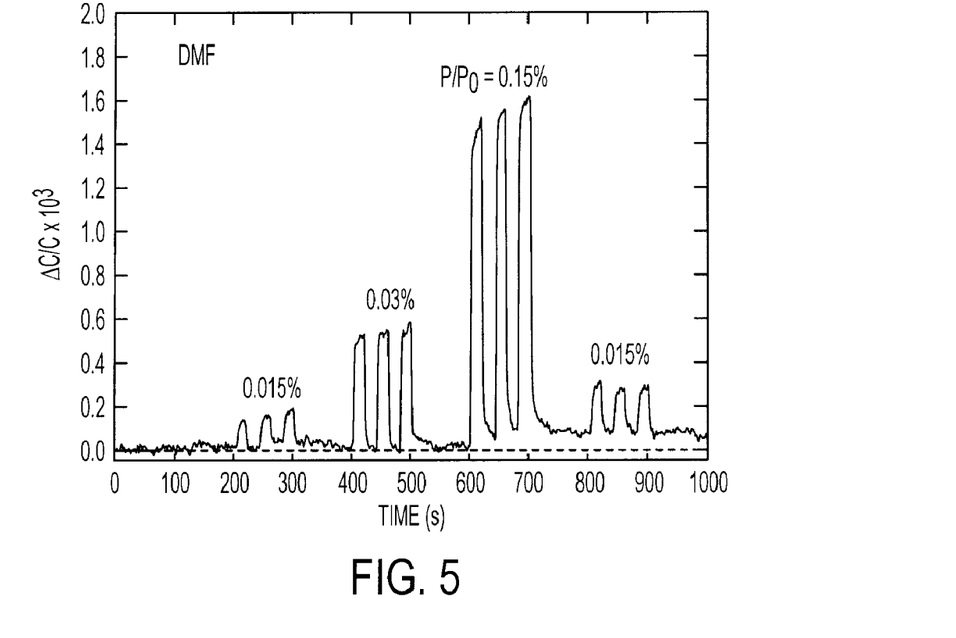
FIG. 5 plots the relative capacitance change of a device in response to repeated 20 s doses of dimethylformamide.

Under an applied bias, fringing electric fields (~$10^5$ to $10^6$ V/cm, for a 0.1 V bias) radiate outward from the SWNTs. These fringing fields are strongest at the SWNT surface and produce a net polarization of the adsorbates that is detected as an increase in capacitance. FIG. 5 plots the relative capacitance change, $\Delta C/C$, of one such device in response to repeated 20 s doses of N,N-dimethylformamide (DMF) at varying values of $P/P_0$. The capacitance was measured using a 0.1 $V_{pp}$, 30 kHz AC voltage applied between the planar back electrode (heavily doped Si substrate) and the SWNT network which was grown on top of a 250 nm-thick thermal oxide. The observed response was rapid (~1 s, currently limited by the vapor delivery system), proportional to the analyte concentration, and completely reversible. (Note that the slow capacitance decay observed after the high-dose exposures was caused by residual DMF desorbing from the vapor delivery system.) Of the chemical vapors tested, a similar, rapid capacitance response to the majority of those vapors that possess an intrinsic dipole moment was observed. The exceptions, such as chlorobenzene, are discussed below. It should be noted that $\Delta C$ is independent of the applied voltage for $V_{AC} < 1$ V, which indicates that polarization is a linear function of the electric field.

EXAMPLE 3

Figure 6:
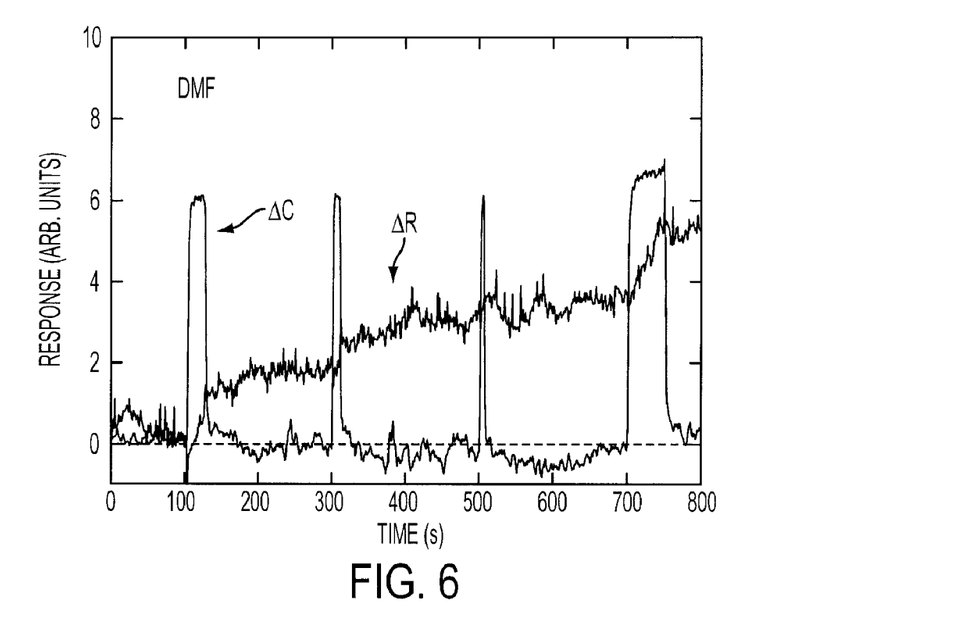
FIG. 6 shows a plot of the resistance and capacitance of a SWNT network.

Capacitance and resistance measurement (DMF and DMMP)—FIG. 6 shows a plot of the resistance and capacitance of a SWNT network measured simultaneously in response to 25, 10, 5 and 50 s doses of DMF. The magnitude of the capacitance response is independent of the delivery time and rises and falls immediately upon the delivery and removal of the DMF. In contrast, the resistance response is much slower and behaves like a dosimeter, integrating the dose of DMF.

Different adsorption sites may have controlled the capacitance and the resistance. The DMF that affects the capacitance desorbs much faster than the DMF that affects the resistance. For the vapors tested the capacitance consistently tracks the vapor concentration in real time whereas the resistance displays a wide range of behavior. For physisorbed molecules the desorption time should be $\ll 1$ s, consistent with the capacitance measurements.

One possible explanation for the slow resistance response is that the DMF affects the resistance predominately at defect sites where the desorption time is abnormally long. Due to the one-dimensional nature of SWNT transport, perturbations at local sites such as defects can cause large changes to the resistance. Defect sites are also likely to have a larger binding energy than the defect-free regions of the SWNT surface. Consequently, the resistance response may be dominated by strongly bound adsorbates at defect sites while the capacitance is dominated by weakly bound adsorbates on the defect-free surface. A slow resistance response was observed for many other analytes indicating that defects or other slowly desorbing sites play an important role in SWNT chemiresistors. Consequently, the capacitance response may provide a better measure of the intrinsic SWNT/adsorbate properties.

Figure 11:
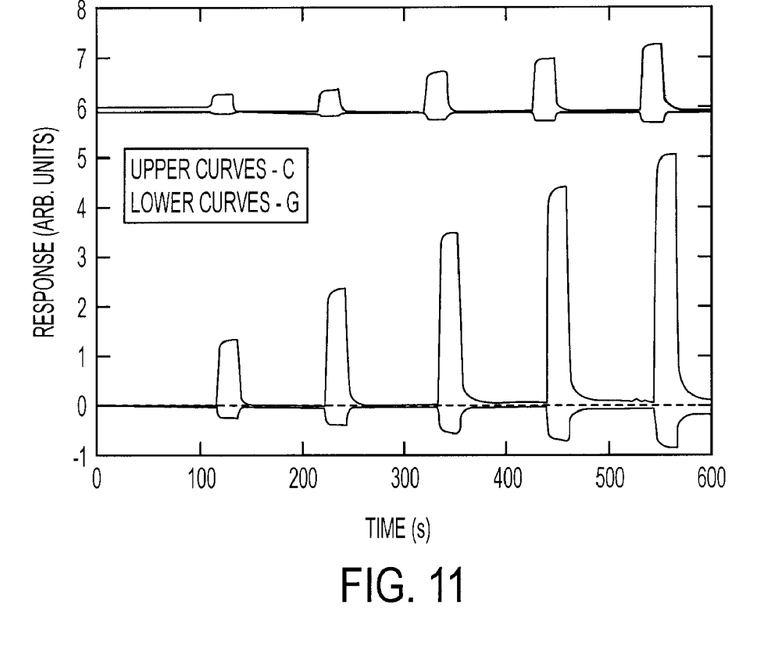
FIG. 11 shows the capacitance (C) and conductance (G) response of a sensor over time while being exposed to increasing concentrations of DMMP.
Figure 12:
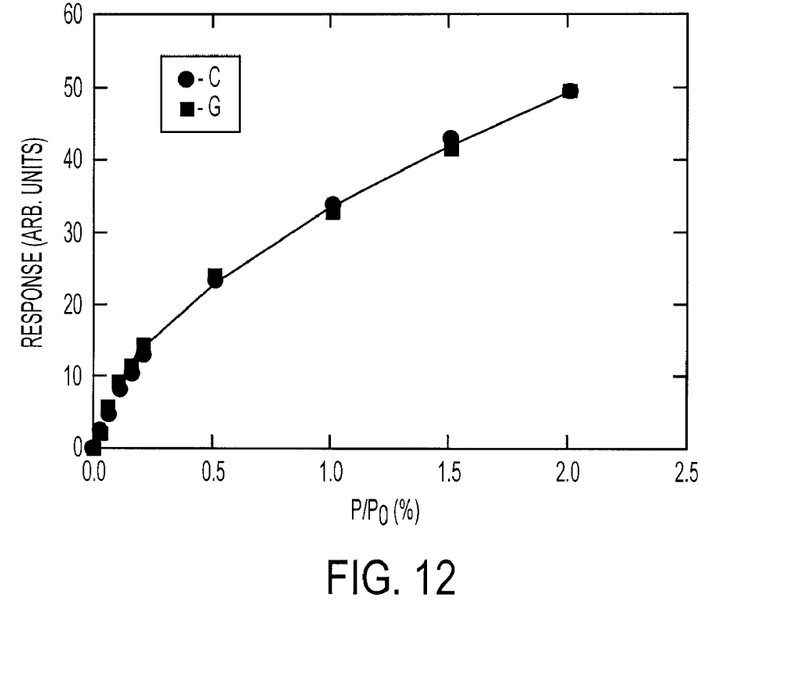
FIG. 12 shows the capacitance (C) and conductance (G) response as a function of concentration.

FIG. 11 shows the capacitance (C) and conductance (G) of a sensor over time while being exposed to increasing concentrations of DMMP. FIG. 12 shows similar data as a function of concentration. The ratio of the change in G to the change in C remained a constant (−12.5%) regardless of the concentration of the exposure.

EXAMPLE 4

Other analytes—In Table 1 for $P/P_0 = 1\%$ is listed the measured values of $\Delta C/C$ along with reported values of $P_0$, $p_{mol}$, and the vapor concentration reported in parts-per-million. Note that analytes with widely different values of $P_0$ but similar dipole moments produce a comparable capacitance response. For example, acetone and dimethyl methylphosphonate (DMMP) produce a comparable capacitance response even though the concentration in the vapor phase differs by over 150 to 1. This observation supports the contention that surface adsorbates are responsible for the capacitance response because for adsorbates in which the interaction with the surface is larger than the intermolecular interaction the surface coverage is proportional to $P/P_0$ rather than the vapor phase concentration.

The magnitude of the capacitance response correlates with the value of the intrinsic dipole moment of the analyte (see FIG. 4). Nonpolar molecules such as hexane and benzene produce a small response, while relatively polar molecules like DMMP and DMF produce a large capacitance response. This correlation with dipole moment holds under the condition that the vapors are each delivered at a constant value of $P/P_0$, and not for a constant value of P. For example, acetone ($\mu = 2.88$ D) and DMMP ($\mu = 3.62$ D) produce a comparable capacitance response when both are delivered at $P/P_0 = 1\%$ even though this condition corresponds to vapor concentrations of 3080 ppm and 16 ppm, respectively. Interestingly, several analytes such as chlorobenzene, 1,2-dichlorobenzene, 2,4-dinitrotoluene, and water produce a small capacitance response even though they possess a relatively large dipole moment. These data indicate that the magnitude of the capacitance response is strongly modified by surface interactions.

TABLE 1

| Chemical Vapor | $P_0$ (mbar) | ppm @ 1% $P/P_0$ | $p_{mol}$ (D) | $\Delta C/C \times 10^3$ @ 1% $P/P_0$ |
|---|---|---|---|---|
| Benzene | 134 | 1360 | 0 | 0.34 |
| Hexane | 200 | 1630 | 0 | 0.42 |
| Heptane | 61 | 618 | 0 | 0.23 |
| Toluene | 38 | 294 | 0.38 | 0.51 |
| Trichlroethylene | 91 | 719 | 0.8 | 0.56 |
| Chloroform | 257 | 2100 | 1.04 | 0.76 |
| Trichloroethane | 29 | 223 | 1.4 | 0.79 |
| Isopropyl alcohol | 56 | 415 | 1.58 | 3.8 |
| Ethanol | 60 | 608 | 1.69 | 3.0 |
| Chlorobenzene | 16 | 122 | 1.69 | 0.4 |
| Methyl alcohol | 168 | 1310 | 1.7 | 2.7 |
| Tetrahydrofuran | 215 | 1740 | 1.75 | 5.9 |
| Ethyl acetate | 126 | 1280 | 1.78 | 3.1 |
| Water | 32 | 243 | 1.85 | 0.5 |
| Dichlorobenzene | 2 | 13.2 | 2.5 | 0.4 |
| Acetone | 304 | 2470 | 2.88 | 6.1 |
| Dimethyl methylphosphonate | 1.6 | 16.2 | 2.9 | 10.2 |
| N,N-dimethylformamide | 5 | 37.5 | 3.82 | 9.3 |

The polarizability of a vapor molecule is given by Eq. (1)

$$\gamma = \gamma_{mol} + \frac{p_{mol}^2}{3kT} \quad (1)$$

Figure 7:
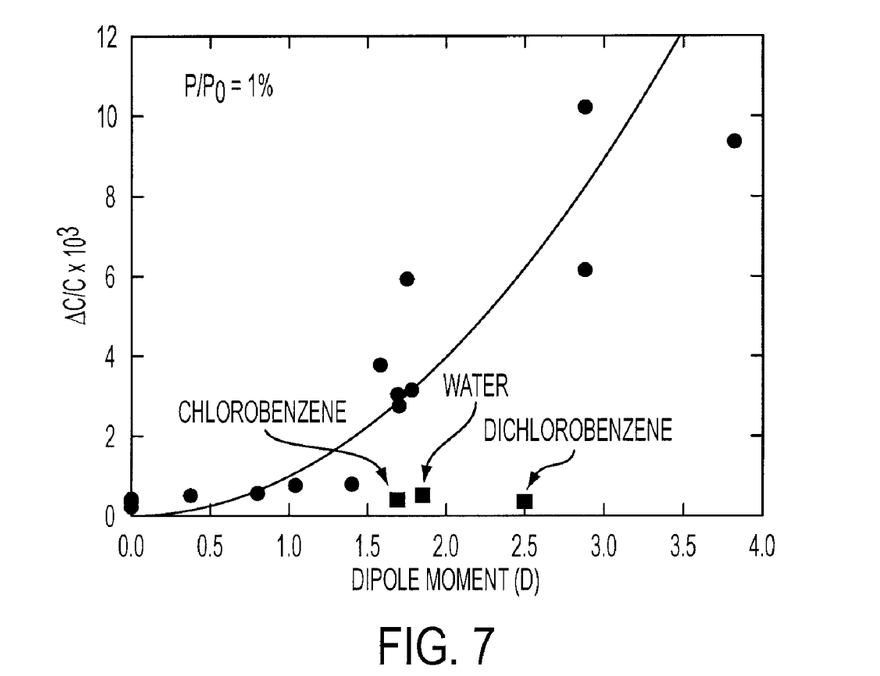
FIG. 7 shows a plot of measured capacitance response to $P/P_0 = 1\%$ doses of various chemical vapors plotted as a function of their molecular dipole moment.

The first term arises from the polarizability, $\gamma_{mol}$, of the molecule and the second term arises from the field-induced alignment of the otherwise randomly oriented molecular dipole moment. Thus, for a dilute vapor the capacitance response should scale as $p_{mol}^2$. The solid line in FIG. 7 is a plot of $\Delta C/C \propto p_{mol}^2$. While there is a general trend toward increased $\Delta C/C$ with increasing dipole moment, it is clear that there are large deviations from this simple model. The deviations are not surprising given that the model applies to free gas molecules and does not include the interaction with the SWNT surface or other adsorbates.

For adsorbed molecules the interaction with the SWNT surface may strongly affect the polarization. The number of adsorbates will depend exponentially on the binding energy of the adsorbate, and this binding energy will be proportional to the applied field. The polarizability of the adsorbate may be quite different from the polarizability of the free gas molecule, and the adsorbate is no longer free to randomly orient but will have preferential orientations that are determined by the interaction with the nanotube surface. Given the complexity of the adsorbate system it is not surprising a simple behavior was not observed. Preliminary density functional calculations indicate that the primary polarization effect derives from the field dependence of the binding energy ($\Delta E_b \sim 1$ meV for $10^6$ V/cm), which causes a change in the number of adsorbates by a factor $\sim \Delta E_b/kT$.

Three notable exceptions to the general trend were chlorobenzene, 1,2-dichlorobenzene, and water, represented by squares in FIG. 7. The solid line is a guide for the eye to show $\Delta C/C \propto p_{mol}^2$. These vapors produce a small capacitance response even though they possess a relatively large dipole moment. Both chlorobenzene and 1,2-dichlorobenzene possess a dipole moment that is oriented in the plane of their benzene ring. For these adsorbates density functional calculations indicate that the lowest energy configuration corresponds to the ring lying flat on the SWNT surface. In this orientation the dipole moment lies perpendicular to the radial electric field, which minimizes the polarization. Water does not share this property; however, its response may be muted by competing adsorption on the adjacent hydrophilic $SiO_2$ surface and by intermolecular interactions that cause the water molecules to cluster. For some analytes such as acetone the primary polarization effect derives from the field dependence of the binding energy, which causes a change in the number of adsorbates by a factor $\sim \Delta E_b/kT$.

The ratio of $\Delta G/\Delta C$ was measured for a variety of compounds. As in the case of DMMP in Example 4, the ratio was found to be constant at different concentrations. Table 2 summarizes these results.

TABLE 2

| Chemical Vapor | DeltaG/DeltaC |
| --- | --- |
| DNT | 20.0% |
| Dichloropentane | 10.0% |
| Nitrobenzene | 7.7% |
| Water | 4.5% |
| Hexane | 4.3% |
| Toluene | 2.5% |
| Benzene | 1.3% |
| IPA | −2.7% |
| Acetone | −3.1% |
| THF | −10.0% |
| DMMP | −12.5% |

EXAMPLE 5

Figure 8:
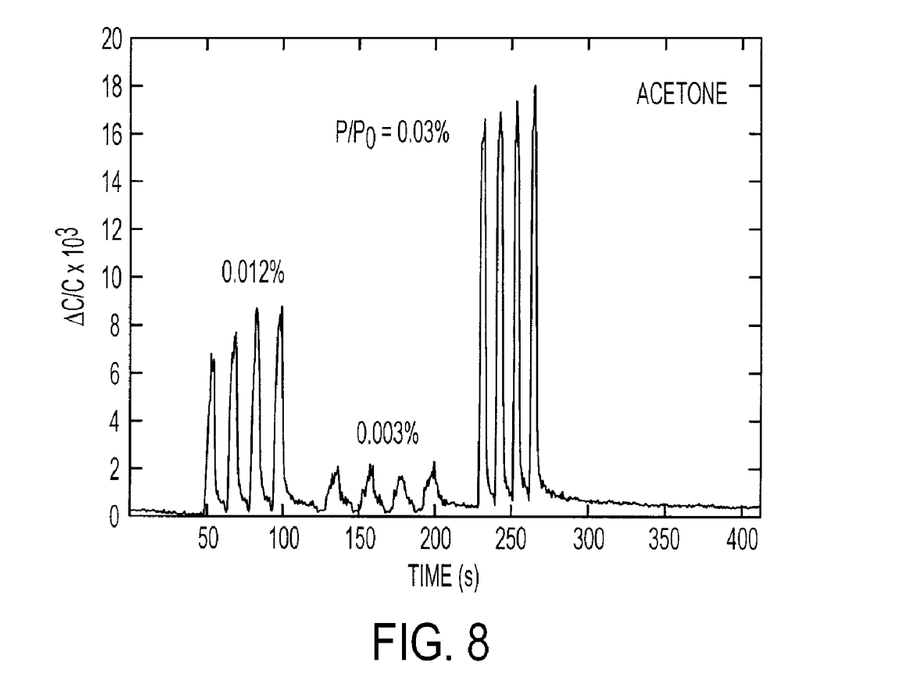
FIG. 8 shows a plot of the response to 10 s doses of acetone of a SWNT chemicapacitor coated with a thin film of the polymer HC.
Figure 13:
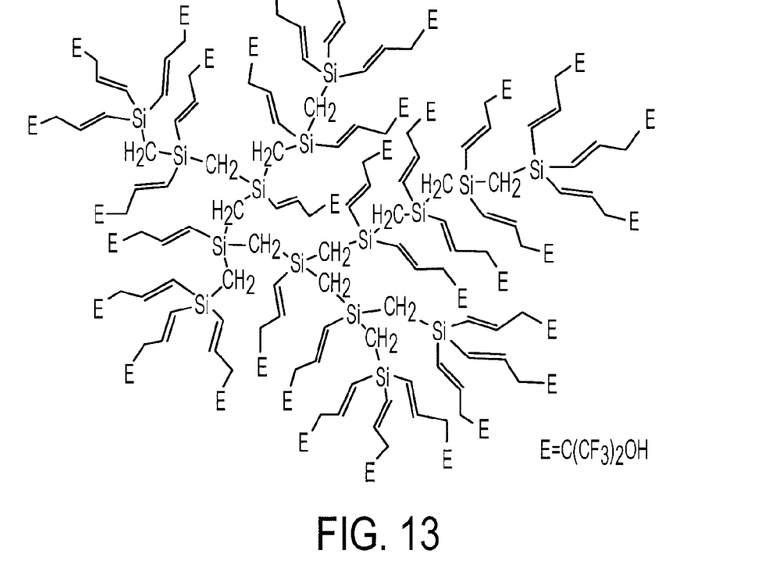
FIG. 13 shows the chemical structure of the polymer HC.

Chemoselectivity—To demonstrate compatibility with chemoselective polymers a sensor was coated with a thin layer (~100 nm) of the polymer HC. HC is a hydrogen-bonding acidic polycarbosilane having a hyperbranched structure, such as shown in FIG. 13. The response of this polymer-coated sensor to 10 s doses of acetone is shown in FIG. 8. This functionalized sensor produces a large, rapid response that is proportional to the concentration of acetone. For a fixed acetone concentration the measured response is approximately 100 times the response measured in the same sensor prior to functionalization. The HC coating concentrates the analyte in the vicinity of the SWNTs increasing the response by a factor of 100 while maintaining a rapid response time.

Figure 9:
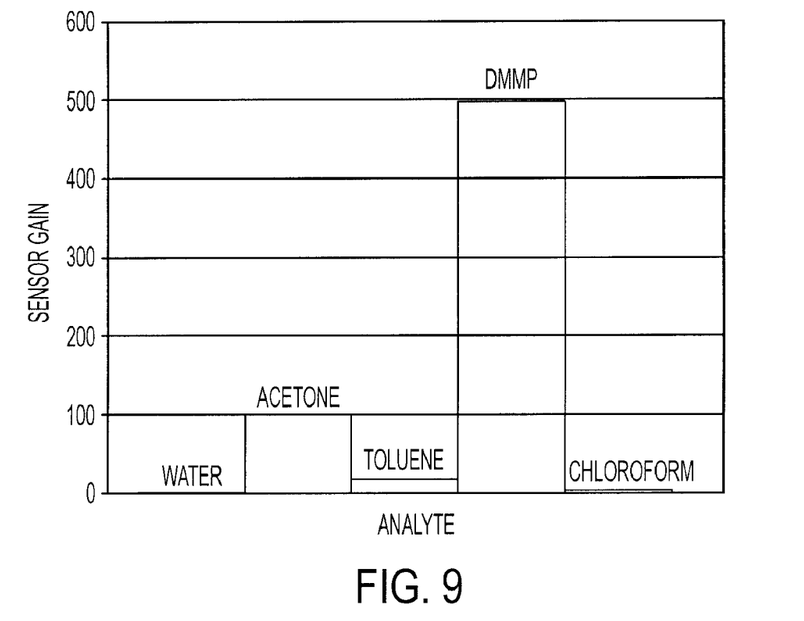
FIG. 9 shows a bar chart of the gain achieved for several analytes using the HC polymer.

FIG. 9 shows a bar graph of the gain observed using the HC coating for five different analytes. The HC coating produces little or no gain for such vapors as water (1×) and chloroform (10×) while producing large gains for acetone (100×) and the nerve-agent simulant, DMMP (500×). By comparing the relative responses of an array of such sensors, each coated with a polymer having different sorption properties, a fingerprint is established that can be used to identify an unknown chemical vapor.

These sensor characteristics compare favorably with commercial chemicapacitors. Using a 3-to-1 signal-to-noise ratio as a detection criterion, it is estimated that MDL=0.5 ppm and $t_{90}$<4 s for acetone and MDL=0.5 ppb and $t_{90}$=370 s for DMMP. For these same analytes, the commercial sensor achieves a MDL=2 ppm and $t_{90}$=228 s for acetone and MDL=2 ppb and $t_{90}$=3084 s for DMMP. The faster response and recovery times may be attributed to the use of a much thinner layer of chemoselective material. For HC, the minimum layer thickness was limited by the tendency of the HC to form a discontinuous film below about 100 nm.

EXAMPLE 6

Chemoselective monolayer—The response time for analytes such as DMMP is limited by diffusion through the layer of HC. Because the SWNT capacitor is based on a surface effect, the time response can be improved and still achieve chemical gain by using extremely thin layers of chemoselective material down to, and including, a single molecular monolayer.

Figure 10:
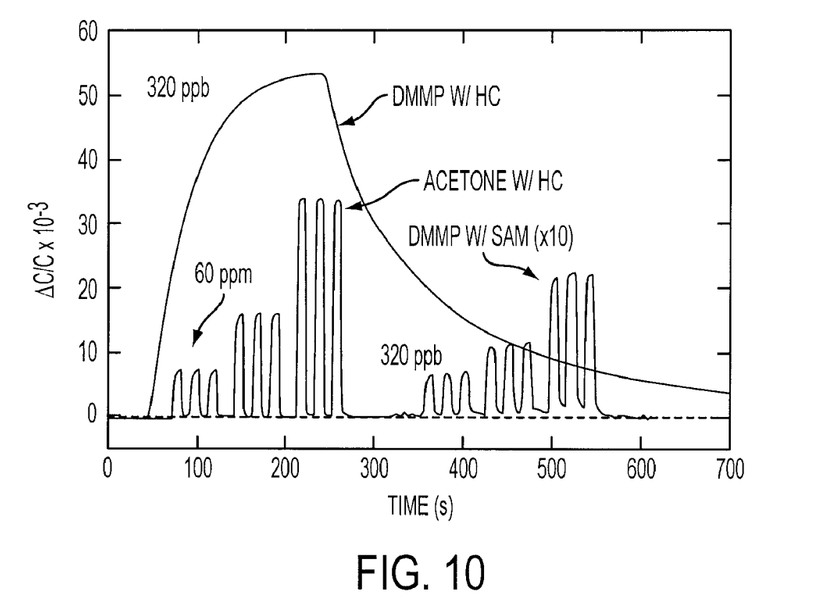
FIG. 10 shows the response of a SAM-coated sensor to repeated 10 s doses of DMMP.

The $SiO_2$ surface was coated with a self-assembled monolayer (SAM) of allylsilanes formed from treatment with allyltrichlorosilane. The terminal alkenes were then reacted with hexafluoroacetone to produce a monolayer of hexafluoroisopropanol groups that partially covered the SWNTs. The response of this SAM-coated sensor to repeated 10 s doses of DMMP ranging from 320 ppb to 2.9 ppm is shown in FIG. 10. The left curve is the response to 10 s doses of acetone of a SWNT chemicapacitor coated with the polymer, HC. The concentration was set at 60, 180, and 540 ppm. The upper curve is the response of the same HC-coated sensor to a single, 200 s dose of DMMP. Note the increased response time caused by the slower diffusion of the DMMP. The right curve is the response (×10) of a SAM-coated sensor to 10 s doses of DMMP. The concentration was set at 320 ppb, 960 ppb, and 2.9 ppm. Note the improvement in response time relative to the HC-coated sensor. For this sensor the response tracks the vapor delivery system indicating that $t_{90}$<4 s, and a MDL=50 ppb was measured. Notably, with the SAM coating the relative capacitance response of DMMP to that of water is increased by a factor of 40 indicating that significant chemically selective gain was achieved.

Obviously, many modifications and variations of the present invention are possible in light of the above teachings. It is therefore to be understood that the claimed invention may be practiced otherwise than as specifically described.

What is claimed is:

1. A sensing device comprising:
 a bottom electrode;
 a dielectric layer on the bottom electrode;
 a grid of nanoelectrodes on and parallel to the dielectric layer;
 a top electrode in electrical contact with the grid; and
 a capacitance meter electrically connected to the top electrode and the bottom electrode.

2. The sensing device of claim 1, wherein the grid of nanoelectrodes is an interconnected network of carbon nanotubes.

3. The sensing device of claim 2, wherein the dielectric layer is porous and has a dielectric constant that changes in response to adsorption of an analyte into the dielectric.

4. The sensing device of claim 2, further comprising:
a material selected from the group consisting of:
- a chemoselective or bioselective accumulator deposited on the carbon nanotubes;
- a chemoselective or bioselective filter deposited on the carbon nanotubes that prevents one or more compounds from contacting the carbon nanotubes; and
- a chemoselective or bioselective functionalizing material that affects the surface chemistry of the carbon nanotubes.

5. The sensing device of claim 2, wherein the carbon nanotubes are single-walled carbon nanotubes.

6. The sensing device of claim 1,
wherein the top electrode comprises a first top electrode and a second top electrode;
wherein the first top electrode and the second top electrode are in electrical contact with the grid; and
wherein the first top electrode is not in direct physical contact with the second top electrode.

7. The sensing device of claim 6, wherein the first top electrode and the second top electrode are interdigitated electrodes.

8. The sensing device of claim 6, further comprising:
an ohmmeter electrically connected to the first top electrode and the second top electrode.

9. The sensing device of claim 6, further comprising:
an AC voltage source electrically connected to the top electrode and the bottom electrode;
an ohmmeter electrically connected to the first top electrode and the second top electrode; and
an AC ammeter electrically connected to the first top electrode and the second top electrode.

10. A method of chemical or biological sensing comprising:
providing a grid of nanoelectrodes;
exposing the grid to fluid suspected of containing one or more chemical or biological analytes; and
measuring a change in the capacitance of the grid with respect to a counter electrode;
wherein the grid is part of a device comprising:
- a bottom electrode;
- a dielectric layer on the bottom electrode;
- the grid on and parallel to the dielectric layer;
- a top electrode in electrical contact with the grid; and
- a capacitance meter electrically connected to the top electrode and the bottom electrode.

11. The method of claim 10, wherein the grid of nanoelectrodes is an interconnected network of carbon nanotubes.

12. The method of claim 11, further comprising the step of:
providing a material selected from the group consisting of:
- a chemoselective or bioselective accumulator deposited on the carbon nanotubes;
- a chemoselective or bioselective filter deposited on the carbon nanotubes that prevents one or more compounds from contacting the carbon nanotubes; and
- a chemoselective or bioselective functionalizing material that affects the surface chemistry of the carbon nanotubes.

13. The method of claim 10, further comprising:
correlating the change in capacitance to the concentration of the analyte.

14. The method of claim 10,
wherein the top electrode comprises a first top electrode and a second top electrode;
wherein the first top electrode and the second top electrode are in electrical contact with the grid; and
wherein the first top electrode is not in direct physical contact with the second top electrode.

15. The method of claim 14, wherein the first top electrode and the second top electrode are interdigitated electrodes.

16. The method of claim 14, further comprising:
measuring a change in the resistance between the first top electrode and the second top electrode.

17. The method of claim 16, further comprising:
correlating the change in resistance and the change in capacitance to the concentration and identity of the analyte.

18. The method of claim 14, further comprising:
applying an AC voltage between the top electrode and the bottom electrode; and
measuring a change in the resistance between the first top electrode and the second top electrode;
wherein measuring the change in capacitance comprises measuring a change in the AC current between the first top electrode and the second top electrode.

19. The method of claim 18, further comprising:
correlating the change in resistance and the change in capacitance to the concentration and identity of the analyte.

* * * * *